(12) United States Patent
Itoh et al.

US006995011B2

(10) Patent No.: US 6,995,011 B2
(45) Date of Patent: Feb. 7, 2006

(54) VECTOR FOR REVERSIBLE GENE INTEGRATION

(75) Inventors: Akira Itoh, Shizuoka (JP); Yutaka Hanazono, Tochigi (JP); Keiya Ozawa, Tochigi (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 376 days.

(21) Appl. No.: 10/188,075

(22) Filed: Jul. 3, 2002

(65) Prior Publication Data

US 2003/0022375 A1    Jan. 30, 2003

(30) Foreign Application Priority Data

Jul. 5, 2001   (JP) .............................. 2001-205236

(51) Int. Cl.
*C12N 15/09*   (2006.01)
*C12N 5/10*   (2006.01)
(52) U.S. Cl. .................................. 435/320.1; 435/325
(58) Field of Classification Search ............... 435/320.1
See application file for complete search history.

(56) References Cited

U.S. PATENT DOCUMENTS 5,629,159 A    5/1997   Anderson

FOREIGN PATENT DOCUMENTS

| EP | 1 083 227 A1 | 3/2001 |
|---|---|---|
| JP | 11-507230 A | 6/1999 |
| WO | WO 96/40877 A1 | 12/1996 |

OTHER PUBLICATIONS

H. Niwa, Rengenerative Medicine and Life Science, vol. 45, No. 13, pp. 2047-2055 (2000) (with English abstract) "A mechanism for differentiation fate determination of ES cells".
N. Nakatsuji, "Human multipotent stem cell lines . . . ", Regenerative Medicine and Life Science, vol. 45, No. 13, pp. 2037-2046 (2000) (with Englsih abstract).
N. Nakauchi, "Analysis of purification and properties . . . " Regenerative Medicine and Life Science, vol. 45, No. 13, pp. 2056-2062 (2000) (with English Abstract).
H. Okano, "Neural stem cells", Regenerative Medicine and Life Science, vol. 45, No. 13, pp. 2063-2077 (2000) (with English Abstract).
K. Fukuda, "Differentiation from marrow-mesenchymal stem cells . . . ", Regenerative Medicine and Life Science, vol. 45, No. 13, pp. 2078-2084 (2000) (with English Abstract).
D. L. Clarke et al., Science, vol. 288, pp. 1660-1663 (Jun. 2, 2000) "Generalized Potential of Adult Neural Stem Cells".
N. Kobayashi et al., Science, vol. 287. pp. 1258-1262 (Feb. 18, 2000) "Prevention of acute liver failure in rats with reversibly immortalized human hepatpcytes".
"Tetracylcine as Regulator of Inducible Gene Expression in Mammalian Cells", Molecular Cloning, Third Ed., Cold Spring Harbor Laboratory Press, pp. 17.52-17.59 (2001).
M. Gossen et al., Proc. Natl. Acad. Sci. USA, vol. 89, pp. 5547-5551 (Jun. 1992) "Tight control of gene expression in mammalian cells by tetracycline-responsive prononters".
M. Gossen et al., Science, vol. 268, pp. 1766-1769 (Jun. 23, 1995) "Transcriptional Activation by Tetracyclines in Mammalian Cells".
S. R. Magari et al., J. Clin. Invest., vol. 100, No. 11, pp., 2865-2872 (Dec. 1997) "Pharmacologic control of humanized gene therapy system implanted into nude mice".
T. Clackson, Curr. Opn. Chem. Biol., vol. 1, pp. 210-218 (1997) "Controlling mammalian gene expression with small molecules".
D. M. Harvey et al., Opn. Chem. Biol., vol. 2, pp. 512-518 (1998) Inducible control of gene expression: prospects for gene therapy.
"Ecdysone as Regulator of Inducible Gene Expression in Mammalian Cells", Molecular Cloning, Third Ed., Cold Spring Harbor Press, pp. 17.71-17.74 (2001).
E. Saez et a., PNAS, vol. 97, No. 26, pp. 14512-14517 (Dec. 19, 2000) Identification of ligands and coligands for the ecdysone-regulated gene switch.
D. No et al., Proc. Natl. Acad. Sci. USA, vol. 93, pp. 3346-3351 (Apr. 1996) "Ecdysone-inducible gene expression in mammalian cells and transgenic mice".
M. Fussenegger et al., Nature Biotechnology, vol. 18, pp. 1203-1208 (Nov. 18, 2000) "Streptoggramin-based gene regulation systems for mammalian cells".
U. Baron et al., Proc. Natl. Acad. Sci. USA, vol. 96, pp. 1013-1018 (Feb. 1999) Generation of conditional mutants in higher eukaryotes by switching between the expressions of two genes.
F. M. V. Rossi et al., Molecular Cell, vol. 6, pp. 723-728 (Sep. 2000) "Transcriptional COntrol: Rheustat Converted to on/off Switch".
A. Hofmann et al., Proc. Natl. Acad. Sci. USA, vol. 93, pp. 5185-5190 (May 1996) "Rapid retoviral delivery of tetracyline inducible genes in a single autoregulatory cassette".

(Continued)

*Primary Examiner*—James Ketter
*Assistant Examiner*—Tara L. Garvey
(74) *Attorney, Agent, or Firm*—Birch, Stewart, Kolasch & Birch, LLP

(57) ABSTRACT

Disclosed is an expression control system with which any gene of interest can be transferred into mammalian cells to thereby change the nature thereof and the gene can be excised at any time by administering a low molecular weight compound to the cells. Specifically disclosed is a vector satisfying specific requirements when inserted into the genome of a mammalian cell.

12 Claims, 6 Drawing Sheets

OTHER PUBLICATIONS

C. Gorman et al., Curr. Opn. Biotech., vol. 11, pp. 455-460 (2000) "Site-specific gene targeting for gene expression in eukaryotes".

F. Buchholz et al., Nature Biotechnology, vol. 16, pp. 657-662 (Jul. 16, 1998) "Improved properties of FLP recombinase evolved by cycling mutagenesis".

B. Sauer, Curr. Opn. Biotech., vol. 5, pp. 521-527 (1994) "Site-specific recombination: developments and applications".

D. Metzger et al., Curr. Opn. Biotech., vol. 10, pp. 470-476 (1999) "Engineering the mouse genone by site-specific recombination".

K. A. Westerman et al., Proc. Natl. Acad. Sci. USA, vol. 93, pp. 8971-8976 (Aug. 1996) Reversible immortalization of mammalian cells mediated by retroviral transfer and site-specific recombination.

E. Saez et al., Curr. Opn. Biotech., vol. 8, pp. 608-616 (1997) "Inducible gene expression in mammalian cells and transgenic mice".

W. Paulus et al., J. Biotech., vol. 81, pp. 159-165 (2000) Variability of transcriptional regulation after gene transfer with the retroviral tetracycline system.

L. St-Onge et al., Nucleic Acids Research, vol. 24, No. 19, pp. 3875-3877 (1996) Temporal Control of the cre recombinase in transgenic mice by tetracycline responsive promoter.

"Tetracycline as Regulator of Inducible", Molecular Cloning, Third Ed., Cold Spring Harbor Press, pp. 17.56-17.57 (2001) LpGene Expression in Mammalian Cells.

R. Pollock et al., PNAS, vol. 97, No. 24, pp. 13221-13226, (Nov. 21, 2000) "Delivery of a stringent dimerizer-regulated gene expression system in a single retroviral nector".

W. Paulus et al., J. Virol., vol. 70, No. 1, pp. 62-67 (Jan. 1996) Self-contained, tetracycline-regulated retroviral vector system for gene delivery to mammalian cells.

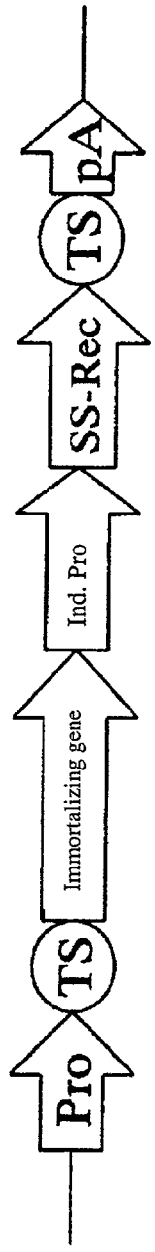
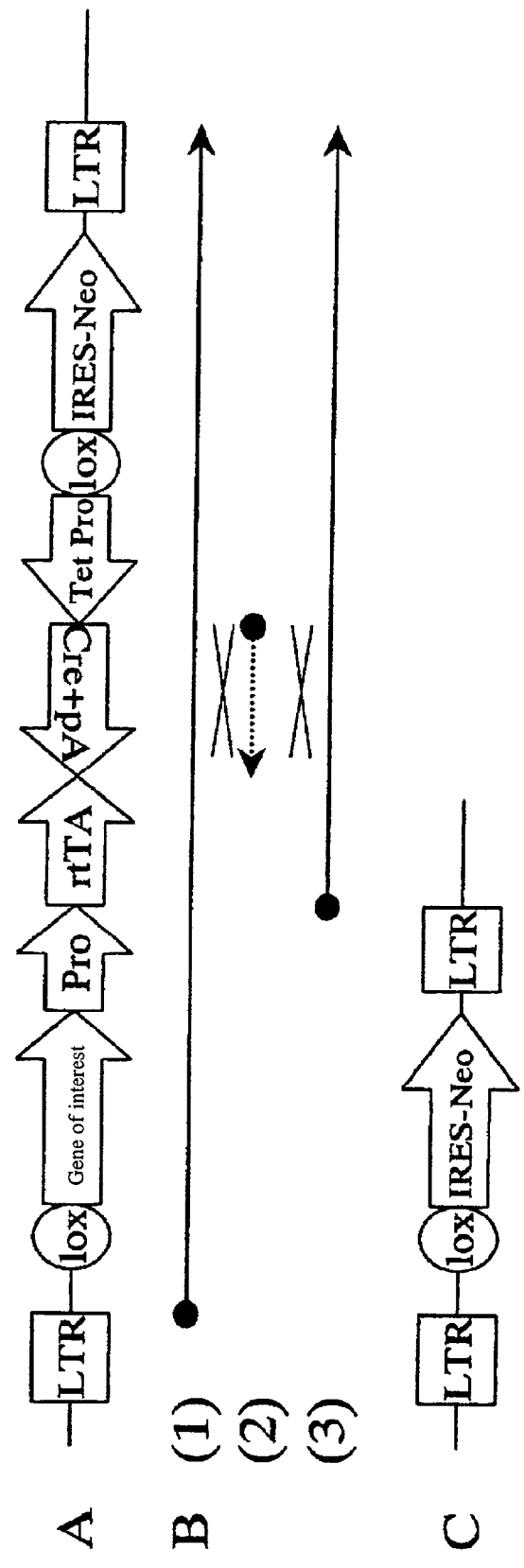
Fig. 1-1 Device of Anderson et al. (Representative Example)
Fig. 1-2 Neutralization of the Expression Leakage of Cre Transcript by Antisense Effect

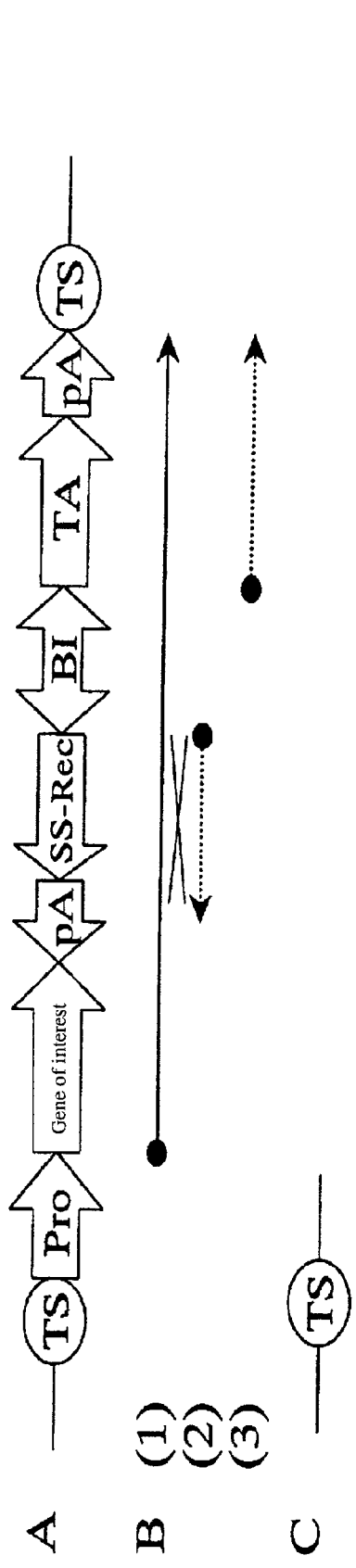
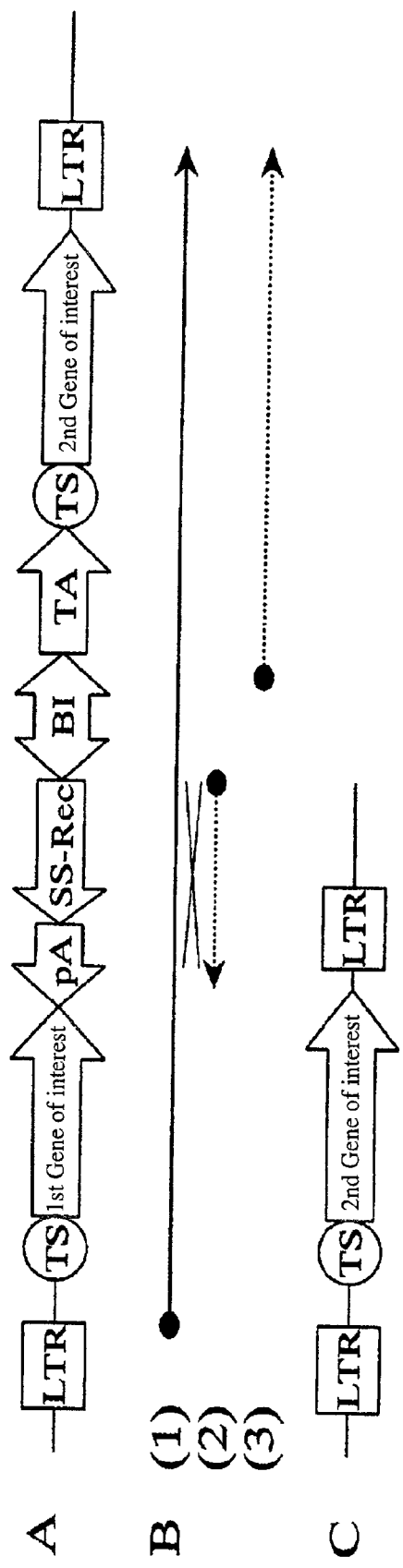
Fig. 2-1 Control by Bidirectional Tet-Responsive Promoter
Fig. 2-2 System using Retrovirus Vector

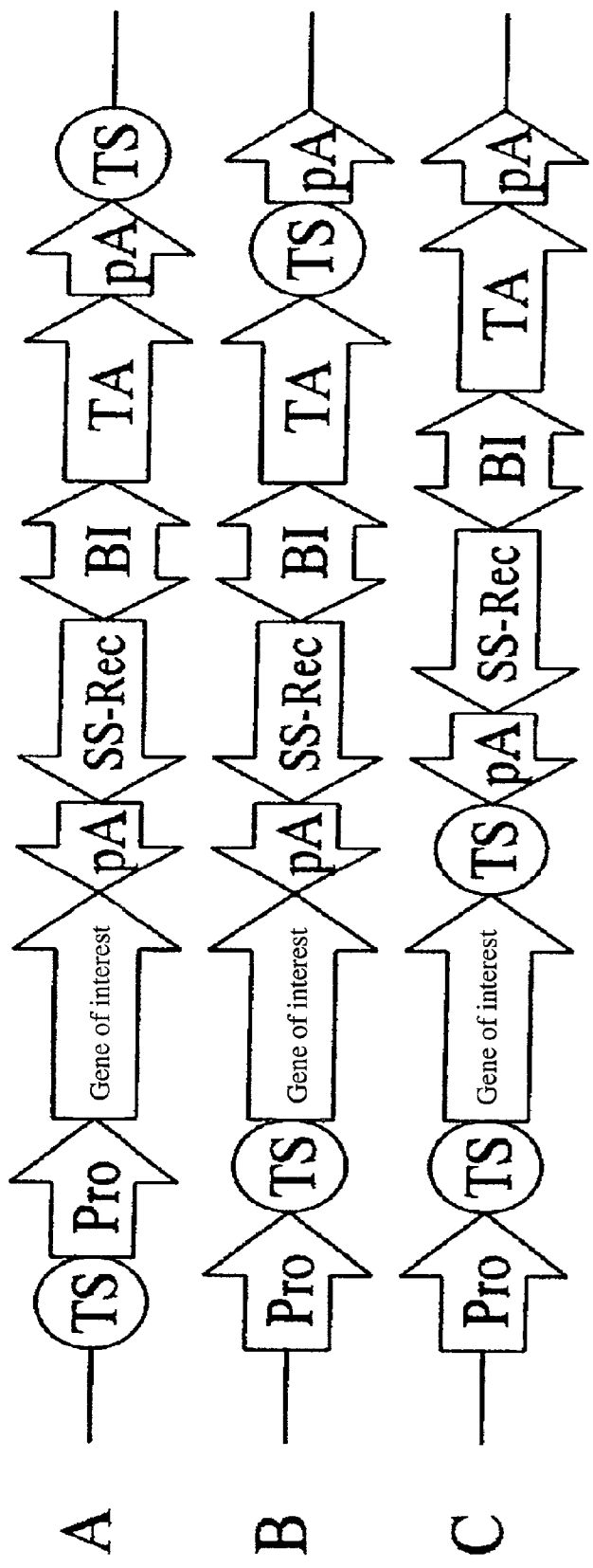
Fig. 3 Control by Low Molecular Weight Compound-Responsive Bidirectional Promoter

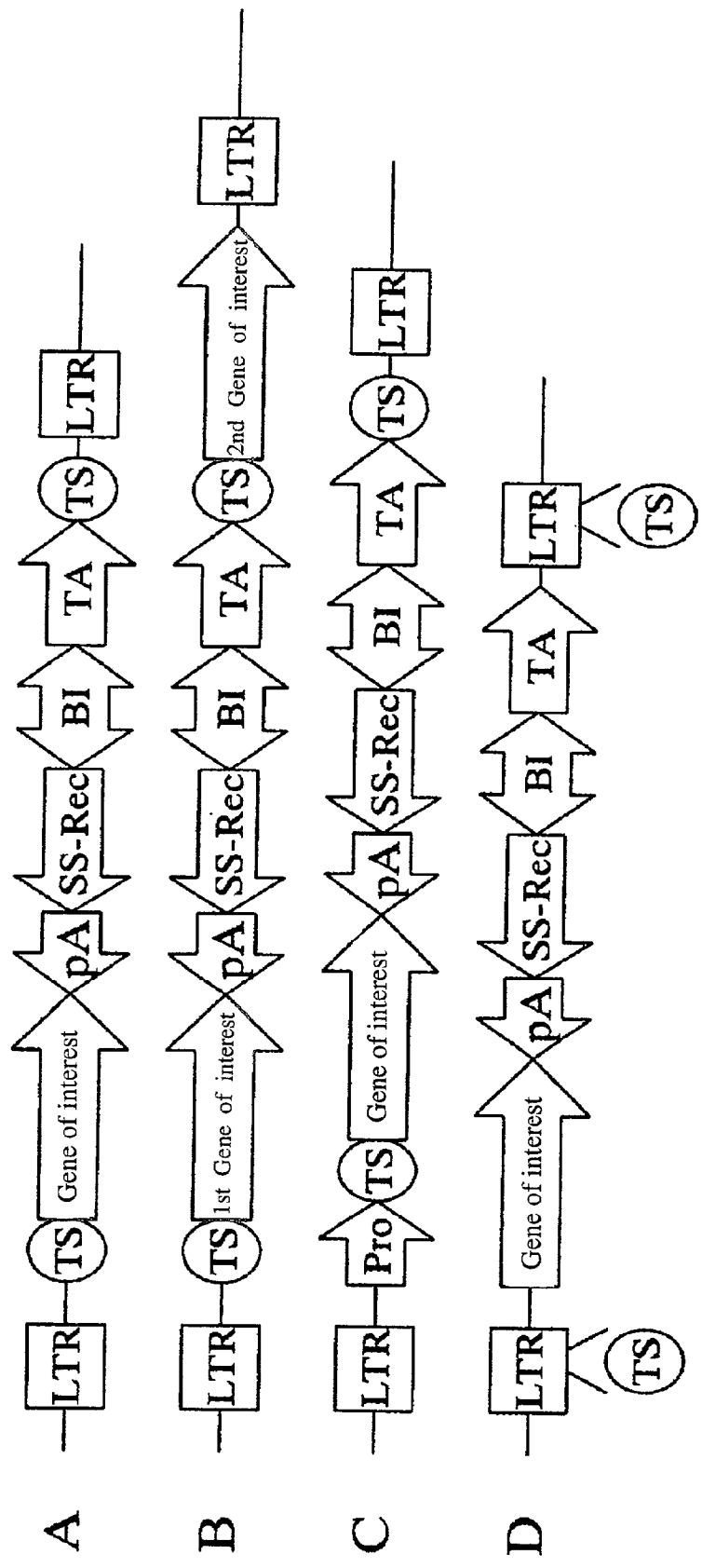
Fig. 4 Systems using Retrovirus Vector

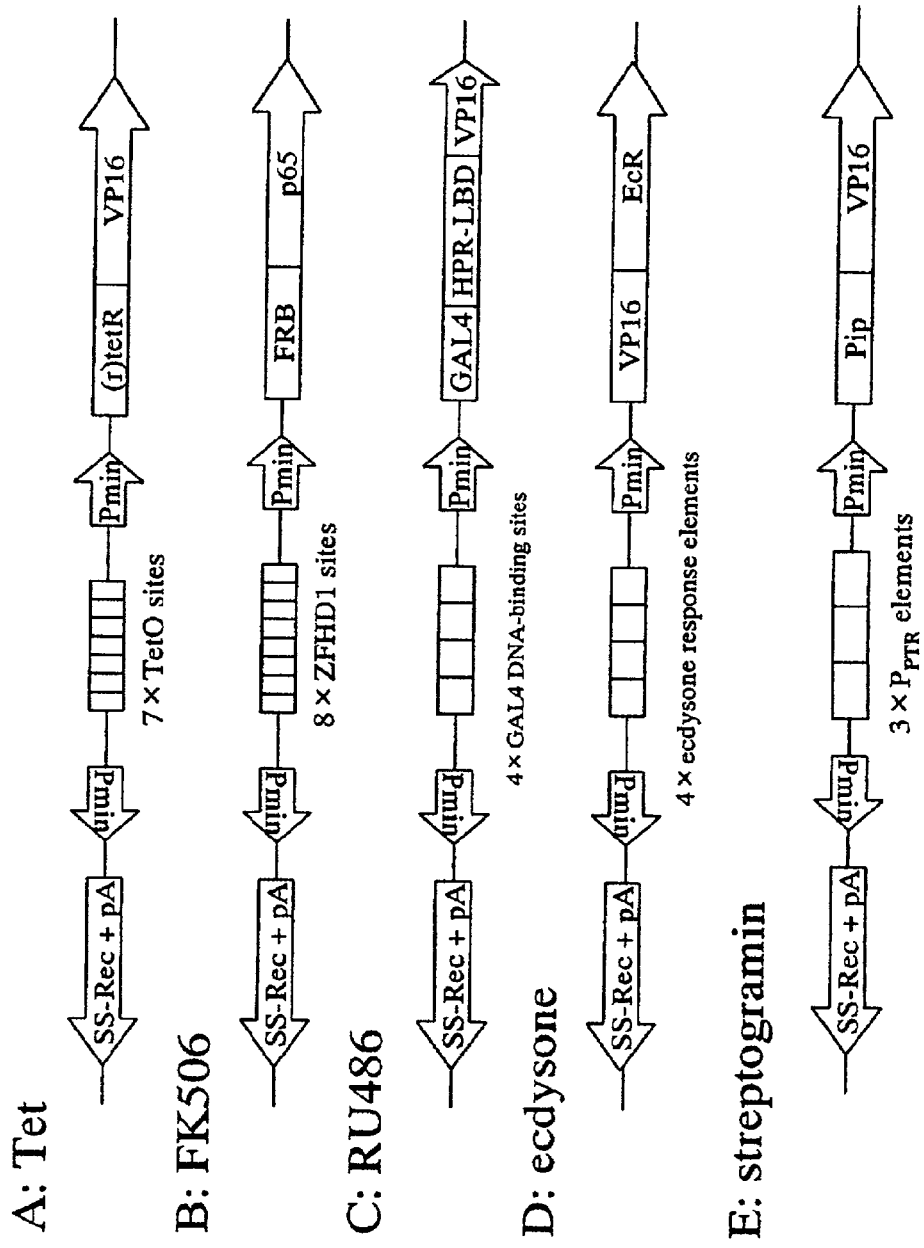
Fig. 5 Low Molecular Weight Compound-Responsive Bidirectional Promoters
A: Tet
B: FK506
C: RU486
D: ecdysone
E: streptogramin

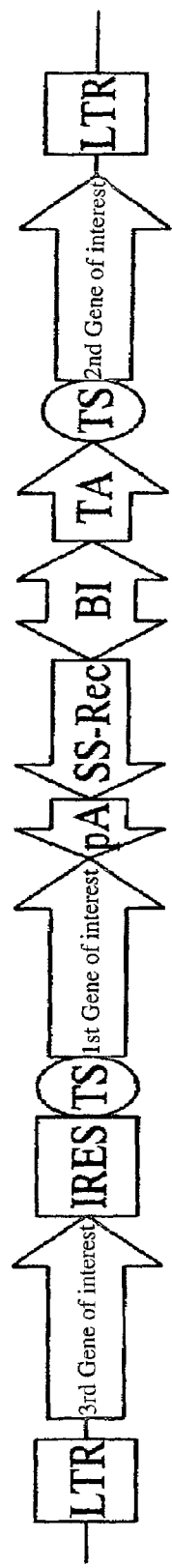
Fig. 6 Combination with Constitutively Expressed Gene

VECTOR FOR REVERSIBLE GENE INTEGRATION

This nonprovisional application claims priority under 35 U.S.C. § 119(a) on Patent Application No. 2001-205236 filed in JAPAN on Jul. 5, 2001, which is herein incorporated by reference.

TECHNICAL FIELD

The present invention relates to a single vector capable of inserting any gene of interest into the genomes of mammalian cells and expressing this gene in those cells, wherein this gene can be excised when necessary by induction using a low molecular weight compound.

BACKGROUND ART

Recently, development of basic sciences, such as developmental biological engineering and stem cell biology, and advances in recombinant vector technologies for gene therapy, etc. have brought about a rapidly growing interest in regenerative medicine. Now, ex vivo and in vivo proliferation and tissue formation technologies are investigated for wide varieties of functional cells and organs including skin, cartilage, bone, blood, blood vessels, nerve, cardiac muscle, pancreatic islets and liver. Details of these investigations are described, for example, in *Regenerative Medicine and Life Science,* Extra Issue to September 2000 Issue of *Protein, Nucleic Acid and Enzyme* (Kyoritsu Shuppan, Co.); *Regenerative Medicine,* Special Issue of *The Medical Frontline* (Saishin Igaku Co.); and *Molecular Medicine,* Vol. 38 No. 1 (Nakayama Shoten).

One of the common problems that regenerative medicine must overcome is the supply of cell sources. The cell sources should be determined by whether they possess the cellular functions required for each target cell, tissue or organ and whether sufficient number of cells can be obtained, i.e., both properties of function and proliferation of the cells are required. At the current technical level, cell sources satisfying these requirements are not obtained sufficiently, except for simple tissues such as skin. Recently, however, induction of proliferation/differentiation of embryonic stem cells (ES cells), induction of proliferation/differentiation of adult stem cells (including those from newborns), and methods for temporarily immortalizing or dedifferentiating terminally differentiated functional cells have attracted attention. ES cells are thought to be able to differentiate totipotently into all cell types/tissues since ES cells can generate individuals. It has been reported that ES cells actually differentiate into diverse cell types in mouse (see the Chapter written by Niwa in *Regenerative Medicine and Life Science,* supra). Since human ES cells have been established recently, application of these cells to medical treatment is expected (see Chapter written by Nakatsuji in *Regenerative Medicine and Life Science,* supra). On the other hand, the presence of various types of stem cells, such as hematopoietic stem cells, neural stem cells and bone marrow mesenchymal stem cells, has been confirmed even in the adult body (see the Chapters written by Nakauchi, Okano and Fukuda in *Regenerative Medicine and Life Science,* supra). Of these, those stem cells other than hematopoietic stem cells are attracting attention as cell sources for, in particular, autologous cell transplantation since ex vivo proliferation technology is applicable to them. Neuronal stem cells are also attracting attention as a cell source for the same purpose since they are capable of differentiating into all germ layers (Clarke et al., *Science* 288:1660). With respect to immortalization of terminally differentiated functional cells, it is reported that human hepatocytes can be rendered proliferative property by transdution of an immortalizing gene and that the cells restore their innate functions as hepatocytes by deletion of the immortalizing gene that may cause cancer (Kobayashi et al., *Science* 287:1258).

In order to improve the proliferation of these cell sources, to induce differentiation into cells of a specific lineage, to control differentiation/dedifferentiation, and to control immortalization/deimmortalization, they have been studied that foreign genes are transduced into cells and that their expressions are controlled. There are known methods for controlling the expression of foreign genes transduced into cells, such as—methods using conditional expression control systems, methods using site-specific recombinases, etc.

The following conditional expression control systems for mammal cells are known: 1) systems using a thermo-sensitive promoter or a thermo-sensitive mutant of a foreign gene; 2) systems using a heavy metal ion-inducible promoter; 3) systems using a hormone-inducible promoter; 4) systems using a hypooxic-inducible promoter; 5) systems using a cytokine-inducible promoter; 6) control systems inducible by tetracycline; 7) control systems inducible by FK506 (also known as rapamycin); 8) control systems inducible by RU486 (also known as mifepristone); 9) control systems inducible by ecdysone; and 10) control systems inducible by streptogramin. The conditional expression control systems described in 1) to 5) above are classic systems, and are not appropriate for controlling gene expression in mammalian cells, because their basal expression levels are rather high and they produce diverse effects on cells other than the control of a target gene.

On the other hand, the conditional expression control systems described in 6) to 10) above were developed recently in order to overcome these problems. For 6), see *Molecular Cloning,* Third Edition, Cold Spring Harbor Laboratory Press, 17.52–17.59 and Gossen et al. (*Proc. Natl. Acad. Sci. USA,* 89:5547–5551 and *Science* 268:1766–1769); for 7), see Magari et al. (*J. Clin. Invest.* 100:2865–2872) and Clackson (*Current Opinion in Chemical Biology* 1:210–218); for 8), see Harvey et al. (*Current Opinion in Chemical Biology* 2:512–518); for 9), see *Molecular Cloning,* Third Edition, Cold Spring Harbor Laboratory Press, 17.71–17.74 Saez et al. (*Proc. Natl. Acad. Sci. USA* 87:14512–14517) and No et al. (*Proc. Natl. Acad. Sci. USA,* 93:3346–3351); and for 10), see Fussenegger et al. (*Nature Biotechnology,* 18:1203–1208).

Among these, control systems inducible by tetracycline are most commonly used. This type of system was developed by Gossen et al. (*Proc. Natl. Acad. Sci. USA,* 89:5547–5551 and *Science* 268:1766–1769). This system, being induced by tetracycline or its derivatives such as doxycycline (hereinafter, collectively referred to as "Tet"), can start (Tet-on) or terminate (Tet-off) the expression of any gene of interest. This mechanism can be explained as follows, taking the Tet-off control system as an example. Briefly, Tet transactivator (tTA) protein forms a complex with an antibiotic Tet (a low molecular weight compound). This complex binds to tandem sequences of Tet-response element (TetO, a 19-mer DNA sequence) to thereby suppress the activity of a minimal promoter located in the vicinity, suppressing the expression of a target gene of interest linked to downstream of the promoter. In the present specification, the combination of the TetO tandem sequences and the minimal promoter is simply referred to as "Tet responsive promoter".

In control systems inducible by tetracycline, an expression system for tTA protein is required in addition to the Tet responsive promoter. Usually, a gene encoding tTA protein is ligated downstream of a constitutive promoter in a separate vector in order to express this protein. The tTA protein is a fusion protein composed of an *E. coli* transposon 10 (Tn10)-derived Tet repressor (TetR) protein that binds to TetO in the absence of Tet and a herpes simplex virus (HSV)-derived VP16 having transcription activating effect. On the other hand, the Tet-on control system employs, instead of the tTA protein, its mutant protein called reverse Tet transactivator (rtTA) protein having 4 amino-acid mutations in the tTA protein. This rtTA protein suppresses the transcriptional activity of the Tet responsive promoter in the absence of Tet, and activates the same in the presence of Tet.

Various improvements have been made to tetracycline-inducible control systems. These improvements include the preparation of a single vector comprising both a control system for a gene of interest and an (r)tTA expression system (Paulus et al., *J. Virol.* 70:62–67); the preparation of mutants of (r)tTA and TetO, as well as a system switching between the expression of two genes depending on Tet concentration (Baron et al., *Proc. Natl. Acad. Sci. USA,* 96:1013–1018); a system that is allowed to have more stringent responsiveness to Tet concentration by a combination of Tet repressor and Tet activator (Rossi et al., *Molecular Cell,* 6:723–728); and a system that is made autoregulatory by expressing under the control of TetO promoter a reporter gene and a DNA encoding tTA bicistronically through an IRES (internal ribosome entry site from encephalomyocarditis virus) placed between the two genes, wherein basal expression levels have been reduced (Hofmann et al., *Proc. Natl. Acad. Sci. USA,* 93:5185–5190).

In expression control systems inducible by low molecular weight compounds other than Tet, the control of expression is performed by a mechanism almost the same as described above (Clackson, *Current Opinion in Chemical Biology,* 1:210–218). Expression control by similar mechanisms is also reported in the references cited above. The term "low molecular weight compound" used herein refers to a low molecular weight organic compound, including tetracycline, FK505, RU486, ecdysone, streptogramin and derivatives thereof.

As site-specific recombinases, several recombinases including Cre recombinase (Gorman et al., *Current Opinion in Biotechnology* 11:455–460) and FLP recombinase (Buchholz et al., *Nature Biotechnology* 16:657–662) have been found. These recombinases belong to the integrase family, and are reported to act in cells or individuals of higher organisms though they are derived from microorganisms (Sauer et al., *Current Opinion in Biotechnology* 5:521–527). Metzger et al. (*Current Opinion in Biotechnology* 10:470–476) reported creation of a transgenic mouse utilizing Cre recombinase; briefly, in order to turn on or turn off the expression of a foreign gene in a specific organ of a transgenic mouse or at any desired time, a first vector in which an organ-specific promoter or inducible promoter is ligated upstream of Cre recombinase gene and a second vector in which a foreign gene or a stuffer sequence preventing the expression of this gene is flanked by two loxP sequences were constructed and transferred into ES cells for creation of a transgenic mouse. FLP recombinase and its recognition sequence FRT are also examined in a similar manner as Cre/loxP are examined (see Westerman et al. cited below).

Westerman et al. constructed a retrovirus vector in which a simian virus-derived immortalizing gene, SV40 large T antigen gene, is flanked by two recognition sites of a site-specific recombinase, and transfected this vector into normal cells. As a result, improved proliferation and life span extension were observed in the cells. They report that by transfecting another retrovirus vector capable of expressing Cre recombinase into these cells, SV40 large T antigen gene can be excised (*Proc. Natl. Acad. Sci. USA* 93:8971–8976). Japanese Unexamined Patent Publication (Kohyo) No. 11-507230 (corresponding to WO96/40877 in which Anderson, David J. is named as an inventor) discloses a cell that has in its genome a structure in which an immortalizing gene is flanked by two target sites of a recombinase, the immortalizing gene being capable of excision by the recombinase. The method described in Japanese Unexamined Patent Publication (Kohyo) No. 11-507230 is a method of gene transfer using the vectors described in FIGS. 3C, 6A and 6B thereof. This method uses a vector in which a recombinase gene is placed downstream of an inducible promoter and, at the same time, an immortalizing gene flanked by two target sites of the recombinase is also placed (see FIG. 1—1 of the present specification). However, a combination of an inducible promoter and a recombinase gene falls within the classic expression control systems described 1) to 5) above, and allows high levels of basal expression (Sasz et al., Current Opinion in Biotechnology, 8:608–616). Even the control systems inducible by a low molecular weight compound described in 6) to 10) do not exert tight control over basal expression. Thus, their drawback is that it is difficult to suspend the expression of recombinase when its expression is not desired.

Taking the tetracycline-inducible control system as an example, the average ratio of [expression level in "on" mode]/[expression level in "off" mode] is only about 100-fold in the Tet-off control system, and only about 10-fold in the Tet-on control system according to Werner Paulus et al. (*J. Biotechnology,* 81:159–165). Therefore, it is difficult to apply these control systems to such a gene whose small amount of basal expression would give an irreversible effect on cells. Specific examples of such a gene include genes causing cytotoxicity, apoptosis-inducing genes, cell differentiation-inducing genes, immortalizing genes, oncogenes, and genes encoding proteins such as site-specific recombinases that cause recombination of nucleic acid sequences. St-Onge et al. (Nucleic Acids Research, 24:3875–3877) actually placed Cre recombinase under control of a tetracycline-inducible control system and examined its action. As a result, they report that leakage of Cre recombinase expression is observed at the basal level. Such leakage of expression at the basal level is the weakest point in low molecular weight compound-inducible control systems, and various researches are made toward its solution (*Molecular Cloning, Third Edition,* Cold Spring Harbor Laboratory Press, p. 17.56). Pollock et al. constructed a retrovirus vector in which a secreted alkaline phosphatase gene is placed under an inducible promoter so that a transcript of this gene from this promoter is sense or antisense to a transcript from the retrovirus vector LTR and an internal promoter; they report that little basal expression was observed in the antisense configuration (*Proc. Natl. Acad. Sci. USA,* 97:13221–13226).

SUMMARY OF THE INVENTION

It is an object of the invention to provide an expression control system having all of the following features: 1) a system by which any gene of interest can be integrated into the genomes of mammalian cells; 2) a system in which the gene of interest can be removed at any time after changing the nature of the cells, by administering a low molecular weight compound to the cells; and 3) a system which can reduce the basal expression levels of such genes whose extremely small amount of expression would give an irreversible influence upon cells, in particular, which can reduce the leakage of a site-specific recombinase transcript to zero. In the case of a single vector comprising a site-specific recombinase, leakage of the recombinase even in an extremely small amount would cause recombination of the vector DNA sequence. Thus, this type of vector is required to satisfy the strictest condition; basal expression should be substantially zero.

The above-mentioned problems can be solved by a single vector containing a group of all the regulatory genes required for enabling i) integration of any gene of interest into the genome of a mammalian cell, ii) expression of the gene in the cell, and iii) when necessary, excision of the gene flanked by two recognition sites of a site-specific recombinase by expression of the recombinase induced by a low molecular weight compound.

The present invention encompasses the following inventions:

(1) A single vector that gives a construction of gene arrangement satisfying all of the following requirements (i) to (iv) when inserted into the genome of a mammalian cell:
  (i) a construct where a DNA encoding a low molecular weight compound-controlled transactivator is placed on one side of a bidirectional promoter responsive to the low molecular weight compound, and a DNA encoding a site-specific recombinase and a polyadenylation signal sequence are placed on the other side of the promoter;
  (ii) a construct where a gene of interest is placed between two target sites of the site-specific recombinase mentioned in (i);
  (iii) a construct where the gene of interest mentioned in (ii) is placed under the control of a promoter capable of directing expression of the gene in mammalian cells, and the DNA encoding a site-specific recombinase mentioned in (i) is placed in such a manner that a transcript from the promoter includes a transcript of the site-specific recombinase DNA, and that the latter transcript and another transcript of the site-specific recombinase DNA from the bidirectional promoter mentioned in (i) form a double-stranded RNA;
  (iv) a construct where polyadenylation signal sequences which are capable of adding poly(A) to a transcript of the low molecular weight compound-controlled transactivator mentioned in (i) and a transcript from the promoter capable of directing expression in mammalian cells mentioned in (iii), respectively, are placed.

(2) A single vector that gives a construction of gene arrangement satisfying all of the following requirements (i) to (iv) when inserted into the genome of a mammalian cell:
  (i) a construct where a DNA encoding a low molecular weight compound-controlled transactivator is placed on one side of a bidirectional promoter responsive to the low molecular weight compound, and a DNA encoding a site-specific recombinase and a polyadenylation signal sequence are placed on the other side of the promoter;
  (ii) a construct where a gene of interest is placed between two target sites of the site-specific recombinase mentioned in (i);
  (iii) a construct where the gene of interest mentioned in (ii) is placed under the control of a promoter capable of directing expression of the gene in mammalian cells, and the DNA encoding a site-specific recombinase mentioned in (i) is placed in such a manner that a transcript from the promoter does not include a transcript of the site-specific recombinase DNA;
  (iv) a construct where polyadenylation signal sequences which are capable of adding poly(A) to a transcript of the low molecular weight compound-controlled transactivator mentioned in (i) and a transcript from the promoter mentioned in (iii), respectively, are placed.

(3) The vector described in (1) above, wherein the vector has the following construction of gene arrangement:
  5'-Target site of the site-specific recombinase-Promoter capable of directing expression in mammalian cells—Gene of interest-Polyadenylation signal sequence placed in the opposite orientation-DNA encoding the site-specific recombinase in the opposite orientation-Low molecular weight compound-responsive bidirectional promoter-DNA encoding the low molecular weight compound-controlled transactivator-Polyadenylation signal sequence-Target site of the site-specific recombinase—3'.

(4) The vector described in (1) above, wherein the vector has the following construction of gene arrangement:
  5'-Promoter capable of directing expression in mammalian cells—Target site of the site-specific recombinase—Gene of interest—Polyadenylation signal sequence placed in the opposite orientation—DNA encoding the site-specific recombinase in the opposite orientation—Low molecular weight compound-responsive bidirectional promoter—DNA encoding the low molecular weight compound-controlled transactivator—Target site of the site-specific recombinase—Polyadenylation signal sequence—3'.

(5) The vector described in (1) above, wherein the vector has the following construction of gene arrangement:
  5'-Promoter capable of directing expression in mammalian cells-Target site of the site-specific recombinase—Gene of interest—Target site of the site-specific recombinase—Polyadenylation signal sequence placed in the opposite orientation—DNA encoding the site-specific recombinase in the opposite orientation—Low molecular weight compound-responsive bidirectional promoter—DNA encoding the low molecular weight compound-controlled transactivator—Polyadenylation signal sequence—3'.

(6) The vector described in any one of (1) to (5) above, wherein the vector is a retrovirus vector.

(7) The vector described in any one of (1) to (5) above, wherein the low molecular weight compound is tetracycline or a derivative thereof, and the low molecular weight compound-controlled transactivator is a reverse tetracycline transactivator.

(8) The vector described in any one of (1) to (5) above, wherein the site-specific recombinase is Cre recombinase, and the target site of the site-specific recombinase is loxP.

(9) The vector described in any one of (1) to (5) above, wherein the site-specific recombinase is FLP recombinase, and the target site of the site-specific recombinase is FRT.

(10) The vector described in any one of (1) to (5), wherein the gene of interest is human telomerase gene and/or Bmi-1 gene.

(11) The vector described in any one of (1) to (5) above, wherein the vector has a construction where a second gene of interest is placed 3' to one of the two target sites of the site-specific recombinase located closer to the 3' end of the vector DNA.

(12) The vector described in (11) above, wherein the vector has the following construction of gene arrangement:

5'-LTR—Target site of the site-specific recombinase—1st Gene of interest—Polyadenylation signal sequence placed in the opposite orientation—DNA encoding the site-specific recombinase in the opposite orientation—Low molecular weight compound-responsive bidirectional promoter—DNA encoding the low molecular weight compound-controlled transactivator—Target site of the site-specific recombinase—2nd Gene of interest—LTR-3'.

(13) Use of the vector described in any one of (1) to (5) above as a vector for gene integration into the genome of a mammalian cell.

(14) A mammalian cell which is transduced with the vector described in any one of (1) to (5) above.

(15) Use of the vector described in any one of (1) to (5) above as a vector for gene therapy.

(16) A transgenic animal which has been created by introducing thereinto the vector described in any one of (1) to (5) above.

BRIEF DESCRIPTION OF THE DRAWINGS

FIG. 1: FIG. 1—1 represents the composition of a vector integrated in the genome of mammalian cells in which a recombinase gene is placed downstream of an inducible promoter, and an immortalizing gene flanked by two recognition sequence of the recombinase is placed in the same vector. FIG. 1-2A shows the composition of a vector designed to neutralize the leakage of expression of a site-specific recombinase transcript by antisense effect in the absence of Tet. FIG. 1-2B shows a diagram of mRNA transcribed from the promoters. FIG. 1-2B(1), (2) and (3) show expressions of the transcripts from the LTR promoter, the Tet responsive promoter, and the internal promoter, respectively. The small amount of basal expression leakage of the transcript from Tet responsive promoter is cancelled by forming a double-strand RNA with transcripts from the LTR promoter and/or the internal promoter. FIG. 1-2C shows the composition of a vector that the vector shown in FIG. 1-2A actually was excised in loxP stuffer after the addition of Tet.

FIG. 2: FIG. 2-1 shows the composition of a vector of the invention used for expression control of a gene of interest by a bidirectional Tet-responsive promoter (A); expressions of the mRNA of the vector-transferred cells in the absence of Tet (B); and the DNA sequence in the cells in the presence of tetracycline (C). FIG. 2—2 shows the composition of a retrovirus vector of the invention used for expression control of a gene of interest by a bidirectional Tet-responsive promoter (A); the mRNA in the vector-transfected cells in the absence of doxycycline (B); and the DNA sequence in the cells in the presence of doxycycline (C).

FIG. 3 illustrates composition of three improved retrovirus vectors (A–C) of the invention used for expression control of a gene of interest by a low molecular weight compound-responsive bidirectional promoter.

FIG. 4 illustrates the composition of four retrovirus vectors (A–D) of the invention using an LTR as a promoter.

FIG. 5 shows examples of the low molecular weight compound-responsive bidirectional promoter, a component of the vector of the invention. Transactivators for A, B, C, D and E are controlled by tetracycline, FK506, RU486, ecdysone and streptogramin, respectively.

FIG. 6 shows the composition of a retrovirus vector of the invention used for allowing constitutive expression of a 3rd gene of interest before and after the excision of stuffer between two target sequences of a site-specific recombinase, separately from the expression of a 1st and a 2nd gene of interest.

DESCRIPTION OF THE PREFERRED EMBODIMENTS

The present invention is characterized by using antisense that reduces basal expression levels; by adapting to an autoregulatory system by placing rtTA under the control of Tet responsive promoter; and by a compact configuration of vector components such as a site-specific recombinase gene, any gene of interest, and recognition sites of the recombinase. It is notable that the vector of the invention comprises a low molecular weight compound-responsive bidirectional promoter as a major component.

First, according to the present invention, leakage of expression of the site-specific recombinase transcript is neutralized by means of antisense. A vector as shown in FIG. 1-2A was constructed. In the 5' to 3' direction in a host genome, a gene of interest is placed downstream of retrovirus vector LTR (long terminal repeat) having promoter activity; then, a gene encoding rtTA is placed downstream of a constitutive, internal promoter; and a gene encoding Cre recombinase is placed under Tet responsive promoter in the opposite orientation relative to the 5'-3' direction of the host genome. It should be noted that what is shown in FIG. 1-2A is the state of the vector when integrated into the genome of a host cell. This means that Cre recombinase gene is placed in such a manner that a transcript of this gene from Tet responsive promoter is antisense against a transcript from the LTR and the internal promoter, as shown in FIG. 1-2B. This configuration was employed based on a hypothesis that, in the absence of Tet, the leakage of Cre recombinase transcript is so small that the amount is cancelled sufficiently. The plasmid vector was constructed and then a retrovirus vector was prepared therefrom, followed by transfection into mammalian cells. However, when the genomic DNA of resultant cells was amplified by PCR (polymerase chain reaction) and subjected to DNA sequencing, it was revealed that cells before addition of Tet have the DNA sequence as shown in FIG. 1-2C, not in FIG. 1-2A. It is considered that this occurred because an extremely small amount of Cre recombinase was expressed at the stage of preparation of the retrovirus vector using a packaging cell strain or at the stage of infecting a target cell with the vector, and excised the loxP stuffer.

From these results, the effect of antisense is not sufficient to apply to Cre recombinase that catalyzes loxP sites within the same vector, though the use of antisense is sufficiently effective for preventing leakage in conventional gene expression. For Cre recombinase, more stringent control is necessary.

Secondly, in addition to the use of antisense, the present invention is characterized by adaptation to an autoregulatory system by placing rtTA under the control of Tet responsive promoter. The expression from Tet responsive promoter becomes "on" only when its TetO tandem sequences bind to a complex between the tetR (Tet repressor) mutant region in rtTA molecule and Tet, and the VP16 region in rtTA molecule activates a minimal promoter in the vicinity. Not only by restricting the amount of Tet, but also by making the amount of rtTA containing transcription activator dependant on Tet responsive promoter, basal expression levels can be reduced. Using this system, Hofmann et al. placed a DNA encoding rTA under the control of Tet responsive promoter through an IRES to thereby reduce basal expression levels (*Proc. Natl. Acad. Sci. USA,* 93:5185–5190).

In addition to the two improvements, i.e., use of antisense to reduce the basal expression levels and adaptation to an autoregulatory system, components necessary for composing the vector of the invention, such as a site-specific recombinase, a gene of interest, recognition sites for the recombinase, etc. are placed in a compact configuration. As a vector skeleton, retrovirus vector may be used. However, when the size of retrovirus vector exceeds approx. 10 kb, it is known that production efficiency decreases. Thus, it is necessary to place vector components in a compact configuration.

The vector of the invention has a wide applicability. Thus, in order to enable the insertion of various genes of interest, it is desirable to minimize the size of its system regulation moiety. As one embodiment of such a vector, the vector as shown in FIG. 2-1 employing a bidirectional Tet responsive promoter (indicated as "BI" in Figures) has been found. In this vector, basal expression of a site-specific recombinase protein is reduced to substantially zero by the synergistic effect of the following two effects: 1) the functioning of a positive feed back system in which a DNA encoding rtTA is placed on one side of a bidirectional Tet-responsive promoter under the control thereof, and 2) the antisense effect produced by formation of double-stranded RNA (i.e., an extremely small amount of transcript expressed at the basal time from a site-specific recombinase gene placed on the other side of the bidirectional Tet-responsive promoter under the control thereof forms double-stranded RNA with a transcript expressed in excess from a separately placed constitutive promoter). Furthermore, 3) the vector does not employ additional elements such as IRES that would increase its size in its control system; instead, it employs TetO (Tet operator sequences) for expressing two genes so that a compact, single vector comprising all the necessary components can be constructed.

The system using the retrovirus vector as shown in FIG. 2-2A expresses the transcripts as shown in FIG. 2-2B. More specifically, this system expresses the transcript (1) stretching from 5' LTR having promoter activity to 3' LTR having polyA signal-adding activity. From this transcript, the protein encoded by 1st gene of interest having an initiation codon and a stop codon is translated. In the absence of Tet, the transcript (3) containing an extremely small amount of rtTA and the transcript (2) containing an extremely small amount of Cre recombinase are expressed due to leakiness of the bidirectional Tet-responsive promoter. However, since the transcript (2) forms double-stranded mRNA with the transcript (1), Cre recombinase protein is not translated. The transcript (3) is translated to an extremely small amount of rtTA protein. When Tet is added to this system, Tet forms a complex with the rtTA protein present in an extremely small amount, and the complex binds to the bidirectional TetO to thereby increase the promoter activity slightly. As a result, the expression levels of rtTA and Cre recombinase are increased. By positive feedback, Cre recombinase protein is translated, which causes loxP-specific recombination to yield the structure as shown in FIG. 2-2C. As a result, 2nd gene of interest is expressed. In order to confirm the action of this system, a red fluorescent protein DsRed having maximum emission at 583 nm (Matz et al., *Nature Biotechnology* 17:969–973) was used as the 1st gene of interest, and a green fluorescent protein EGFP having maximum emission at 507 (Chalfie et al., *Science* 263:802–805) was used as the 2nd gene of interest in the vectors described in Examples 1 to 4 for easy detection of expression. By using DsRed and EGFP in combination, cells infected with this retrovirus vector assume red fluorescence from DsRed, and those cells in which the loxP stuffer containing DsRed gene has been excised by the Tet-induced expression of Cre recombinase no longer assume red fluorescence but assume green fluorescence from EGFP.

Retrovirus vectors were produced from the plasmid vectors prepared according to the methods as described in Examples 1 to 3, followed by transfection into mouse NIH3T3 cells. As a result, it was confirmed that cells assume red fluorescence from DsRed in the absence of doxycycline, and that they assume green fluorescence upon addition of doxycycline. Subsequently, the nucleotide sequence from the vector integrated into the NIH3T3 cell genome was analyzed according to the method as described in Example 4. As a result, a DNA sequence of the genetic structure as shown in FIG. 2-2A was confirmed in the absence of doxycycline, and a DNA sequence of the genetic structure as shown in FIG. 2-2C was confirmed after the addition of doxycycline.

From these results, it was confirmed that such vectors could solve the problems for solution of the invention (i.e., to provide a vector that can transfer any gene of interest into mammalian cells to thereby change the nature thereof, wherein the gene can be excised at any time by administering a low molecular weight compound to the cells). Thus, the present invention has been completed. According to the single vector of the invention, (1) it is possible to integrate any gene of interest into the genomes of mammalian cells and express the gene in those cells; (2) the gene flanked by two recognition sites of a site-specific recombinase can be excised when necessary by a small molecular weight compound-induced expression of the recombinase; and (3) a single vector contains an entire group of genes that regulate these functions. Although a method of excising any gene of interest by activating a site-specific recombinase through induction by a low molecular weight compound is an ideal system, no success has been reported to date. This system has been completed by the present invention for the first time.

The present invention relates to the following two single vectors (a) and (b) that give construction of gene arrangement satisfying all the requirements described in (1) to (4) below, respectively, when integrated into the genome of a mammalian cell.

(a) A single vector that gives a construction of gene arrangement satisfying all of the following requirements (1) to (4) when inserted into the genome of a mammalian cell:

(1) a construct where a DNA encoding a low molecular weight compound-controlled transactivator is placed on one side of a bidirectional promoter responsive to the low molecular weight compound, and a DNA encoding a site-specific recombinase and a polyadenylation signal sequence are placed on the other side of the promoter;

(2) a construct where a gene of interest is placed between two target sites of the site-specific recombinase mentioned in (1);

(3) a construct where the gene of interest mentioned in (2) is placed under the control of a promoter capable of directing expression of the gene in mammalian cells, and the DNA encoding a site-specific recombinase mentioned in (1) is placed in such a manner that a transcript from the promoter includes a transcript of the site-specific recombinase DNA, and that the latter transcript and another transcript of the site-specific recombinase DNA from the bidirectional promoter mentioned in (1) form a double-stranded RNA;

(4) a construct where polyadenylation signal sequences which are capable of adding poly(A) to a transcript of the low molecular weight compound-controlled transactivator mentioned in (1) and a transcript from the promoter capable of directing expression in mammalian cells mentioned in (3), respectively, are placed.

(b) A single vector that gives a construction of gene arrangement satisfying all of the following requirements (1) to (4) when inserted into the genome of a mammalian cell:

(1) a construct where a DNA encoding a low molecular weight compound-controlled transactivator is placed on one side of a bidirectional promoter responsive to the low molecular weight compound, and a DNA encoding a site-specific recombinase and a polyadenylation signal sequence are placed on the other side of the promoter;

(2) a construct where a gene of interest is placed between two target sites of the site-specific recombinase mentioned in (1);

(3) a construct where the gene of interest mentioned in (2) is placed under the control of a promoter capable of directing expression of the gene in mammalian cells, and the DNA encoding a site-specific recombinase mentioned in (1) is placed in such a manner that a transcript from the promoter does not include a transcript of the site-specific recombinase DNA;

(4) a construct where polyadenylation signal sequences which are capable of adding poly(A) to a transcript of the low molecular weight compound-controlled transactivator mentioned in (1) and a transcript from the promoter mentioned in (3), respectively, are placed.

One embodiment of the vector construction of the invention is shown in FIG. 3. FIG. 3 is a schematic representation of the vector when integrated into the genome of a target cell. As a method of gene transfer, a circular plasmid is linearized with restriction enzymes and then introduced into cells by various methods such as the calcium phosphate method, electroporation and lipofection. Details of these methods are described in Chapter 16 in Sambrook et al., *Molecular Cloning, Third Edition,* Cold Spring Harbor Press. The locations of the recognition sequences of a site-specific recombinase may vary in a number of ways including the examples shown in A to C in FIG. 3 as long as they are placed with a gene of interest between them. Preferably, the vector of the invention is a vector that has an action of allowing itself to be integrated into the host genome. Specific examples of this type of vector are retrovirus vectors that are obtained by improving viruses belonging to the family Retroviridae for use in gene transfer. The retrovirus vector has strong enhancer and promoter activities in the 5' LTR itself, and the promoter indicated in FIG. 3 may be substituted by the LTR. Thus, it is not necessarily required to insert a new promoter. Further, the 3' LTR has poly(A) addition signal activity and thus it is not necessary to insert a new polyadenylation signal sequence. FIG. 4 illustrates some possible configurations. The vectors used in the following Examples derived from mouse stem cell virus (MSCV) belonging to the genus *Oncovirus* are capable of transferring genes at a relatively high rate into those cells which are generally low in gene transfer efficiency (such as hematopoietic stem cells) (Kaneko et al., *Human Gene Therapy,* 12:35–44). The genus *Lentivirus* is included in Retroviridae, and the viral genome of its members has an action of allowing itself to be integrated into the host genome. *Lentivirus*-derived *lentivirus* vectors are included in the concept of the retrovirus vector of the invention. *Lentivirus* vectors have the advantage of being capable of transferring genes even into non-dividing cells and the expression of transferred genes are stable for a long period of time (Vigna, *The Journal of Gene Medicine* 2:306–316). Thus, they are preferable as the vector of the invention. However, because the promoter activity of the LTR of *Lentivirus* is lower than that of *Oncovirus,* it is therefore desirable to place an internal promoter as shown in FIG. 4C separately. The central DNA flap of *Lentivirus* has an action of transporting the vector into the nucleus of the host cell, and is reported to enable gene transfer at high efficiency into a group of cells that are difficult to infect with other virus vectors (Sirven et al, *Blood* 96:4103–4110). This central DNA flap may be inserted into the vector of the invention. Further, it is also possible to insert the target sequences of a site-specific recombinase into the retrovirus LTRs, respectively, as shown in FIG. 4D (Cossu et al., *Human Gene Therapy* 10:1607–1617). In this case, one target sequence of the site-specific recombinase may be inserted into the U3 region of the 3' LTR at the time of preparation of the retrovirus vector plasmid; then, when the vector is integrated into the host cell genome, the LTR on both ends includes 3' LTR-derived U3 region and thus the target sequence of the recombinase is simultaneously inserted (Coffin et al., *Retroviruses,* pp. 438–439, Cold Spring Harbor Laboratory Press). Adeno-associated virus (AAV) belonging to Parvoviridae also has a nature of being integrated into the host genome. AAV-derived vectors are capable of gene transfer into non-dividing cells and are highly safe (Smith-Arica et al., *Curr Cardiol* Rep., 3:43–49). Thus, they are useful as the vector of the invention.

The packaging cell strain to be used in the production of retrovirus vectors is not particularly limited. For example, packaging cell strains that may be used are listed in Table 1, Chapter 9, in J. M. Coffin, S. H. Hughes & H. E. Varmus (eds.), *Retroviruses,* Cold Spring Harbor Laboratory Press. Cell strains appropriate for target animal species may be selected by reference to the range of hosts indicated in Table 2 in the same book. Recently disclosed packaging cell strains, such as Bing (Thony et al, *Human Gene Therapy* 7:1587–1593) and Phoenix (Grignari et al., *Cancer Research* 58:14–19), may also be used.

With respect to promoters responsive to a low molecular weight compound, expression control systems inducible by tetracycline, FK506, RU486, ecdysone, streptogramin and derivatives thereof have been described earlier in the present specification. The principles of these expression control systems have a common mechanism. That is, the transactivator comprises the three components of a binding site for a low molecular weight compound, a binding site for a DNA element, and a transcription activating region; when a complex between the transactivator protein and the low molecular weight compound binds to the DNA element placed upstream of a minimal promoter, the transcription activating region in the transactivator protein activates or inhibits the minimal promoter in the vicinity. A low molecular weight compound-responsive bidirectional promoter, which is a major element of the single vector of the invention, is composed of a DNA element flanked by two minimal promoters, and is applicable to promoters responsive to low molecular weight compounds other than tetracycline (see FIG. 5).

A DNA encoding the transactivator protein is ligated on one side of the above-described bidirectional inducible promoter, and a DNA encoding a site-specific recombinase is ligated on the other side of this promoter. When the transactivator protein is a heterodimer composed of a protein having a binding site for the DNA element and a protein having a transcription activating region, a gene encoding either one of these protein subunits may be ligated to the promoter. Alternatively, a plurality of genes or all of the genes encoding the protein subunits may be ligated through an IRES. For example, in the system using an FK506-responsive promoter, the transactivator protein is composed of the following two fusion proteins: a fusion protein between FK506-binding protein (FKBP) and ZFHD1 protein that binds to DNA element sequences (Pomerantz et al., *Science* 267:93–96) and a fusion protein between FKBP12-rapamycin-binding (FRB) protein that binds to FKBP (Choi et al., *Science* 273:239–242) and NFκB p65 having a transcription activating region. The heterodimerization of these fusion proteins through FK506 activates the minimal promoter in the vicinity (Rivera et al., *Nature Medicine* 2:1028–1032). In this system, a DNA encoding one of the fusion proteins, preferably the FRB-p65 fusion protein having a transcription activating region, or a DNA encoding both fusion proteins with an IRES placed between them, may be ligated downstream of the bidirectional FK506-responsive promoter shown in FIG. 5B on one side of the promoter.

Transactivator proteins for RU-486-, ecdysone- and streptogramin-responsive promoters are a fusion protein composed of yeast GAL4, the ligand binding region of human progesterone receptor and VP16; a heterodimer composed of human RXRα and a VP16-ecdysone receptor fusion protein; and a fusion protein composed of *Streptomyces* Pip protein and VP16, respectively. With respect to the streptogramin-responsive promoter, two ways of control are reported: "PipOff" where expression is inhibited by the action of this antibiotic and "PipOn" where expression is activated by it (Fussenegger et al., *Nature Biotechnology* 18:1203–1208). Since "PipOn" is a control method that does not employ a transactivator having a transcription activating domain, the present invention is not applicable thereto.

Improvements to tetracycline transactivator toward still tighter control have been reported (Urlinger et al., *Proc. Natl. Acad. Sci. USA*, 97:7963–7968). These improvements include 1) replacement of VP 16 (a transcription activating region contained in tTA and rtTA) with a synthetic enhancer; 2) introduction of two to five mutations into the amino acid sequence of rtTA; and 3) alteration of the DNA sequence according to the codon use in humans. The improved rTA and rtTA may be used preferably as the low molecular weight compound-controlled transactivator used in the invention.

As a minimal promoter in the low molecular weight compound-responsive promoter, any promoter may be used as long as it has the function as a minimal promoter. For example, promoters, such as CMV hyperacute stage promoter (Depto et al., *J. Virol.* 63:1232–1238), insect heat shock promoter (Pellicer et al., *J. Biol. Chem.* 259:14812–14817), interleukin 2 promoter (Rivera et al., *Nature Medicine* 2:1028–1032) and herpes simplex virus thymidine kinase promoter (Abruzzese et al., *Molecular Therapy* 2:276–287), that lack at least the enhancer region, have TATA sequences and satisfy requirements for the functioning of RNA polymerase II may be used. Further details are described in *Molecular Biology of the Cell, 3rd Edition*, pp. 421–423, Newton Press.

With respect to site-specific recombinases, the integrase family including Cre recombinase and FLP recombinase has been already mentioned. Cre recombinase in combination with its target sequence loxP and FLP recombinase in combination with its target sequence FRT may be used for equal purposes. Both recombinases may be used as the site-specific recombinase of the invention. According to the report of Westerman et al. (*Proc. Natl. Acad. Sci. USA*, 93:8971–8976), both of these recombinases were capable of achieving the intended site-specific recombination, and the recombination efficiency was higher when Cre recombinase was used. The single vector of the invention comprises a gene for a site-specific recombinase and its target sequences within the same vector. Therefore, compared to gene transfer using two separate vectors comprising target sequences and a site-specific recombinase gene, respectively, gene transfer using the vector of the invention is less influenced by recombination efficiency since target sequences and the recombinase gene are introduced into cells simultaneously. Thus, either of the site-specific recombinases may be used. However, it is preferable to use Cre recombinase with its target sequence loxP because of its sensitivity in reaction.

The optimum temperature of FLP recombinase is around 30° C. In particular, the recombinase (FLP-F70L) derived from plasmid pOG44 (available from Stratagene or Invitrogen) has a point mutation in its amino acid sequence and thus its enzyme activity is reported to be clearly low at 37° C., which is a commonly employed temperature for culturing mammalian cells (Buchholz et al, *Nucleic Acids Research*, 24:4256–4262). Therefore, when the activity of Cre recombinase is too sensitive and causes unintended excision of loxP stuffer, a combination of the mutant FLP and FRT may be used depending on the target cell and the gene of interest. In that case, cells are preferably cultured at around 37° C. at which the FLP recombinase activity is low. At the time when the excision of FRT stuffer is desired, the temperature may be shifted to around 30° C. simultaneously with the addition of a low molecular weight compound. The term "stuffer" used herein means a nucleotide sequence flanked by two recognition sequences of a site-specific recombinase.

On the other hand, Cre/loxP system is a widely applicable technology and used effectively, for example, in the production of packaging cells for retrovirus vectors (Arai et al., *J. Virol.* 72:1115–1121). When it is desired to use a Cre/loxP containing vector in combination of the vector of the invention, FLP/FRT system or some other member of the integrase family may be selected as a component of the vector of the invention.

As one feature of the present invention, the vector of the invention can express a 2nd gene of interest after excision of a 1st gene of interest. This is enabled by placing the 2nd gene of interest 3' to one of the two target sites of a site-specific recombinase located closer to the 3' end of the vector DNA. For this purpose, a marker gene for confirming the excision of the 1st gene of interest may be placed in the vector. Alternatively, a drug resistance gene for applying a selection pressure may be place therein. In the following Examples, expression of EGFP gene (a 2nd gene of interest) is confirmed after excision of DsRed gene (a 1st gene of interest) to demonstrate the action of this system. This means that the vector of the invention may be used as a switching vector. Furthermore, considering the use of the vector of the invention in the fields of regenerative medicine and cell transplantation therapy where some problem might occur in those cells which were transplanted or mixed into the body, the vector may comprise a suicide gene that kills those cells selectively. Specific examples of a suicide gene useful in the vector include Fas gene inducing apoptosis and the thymidine kinase gene of herpes simplex virus. Further, as a vector for gene therapy, the vector of the invention is capable of expressing a gene encoding a therapeutic enzyme or an anti-tumor protein under induction by a low molecular weight compound. As one example of this use, a gene encoding a protein that recognizes tumor cells (e.g., a single chain antibody to ErbB, or its ligand EGF) may be placed in the vector as a 1st gene of interest, and a gene encoding TNF or a cytokine may be placed as a 2nd gene of interest.

Furthermore, in addition to a 1st and a 2nd gene of interest, it is also possible to allow constitutive expression of a 3rd gene of interest before and after the stuffer excision. When the configuration of genes shown in FIG. 6 is used, the 3rd gene of interest and the 1st gene of interest are expressed before stuffer excision, and the 3rd gene of interest and the 2nd gene of interest are expressed after the stuffer excision. If herpes simplex virus thymidine kinase gene is placed as a 3rd gene of interest, it is possible to induce all of the vector-transfected cells to suicide by addition of ganciclovir (an antiviral drug), irrespective of the expression of the 1st or the 2nd gene of interest.

The gene of interest useful in the invention is not particularly limited, and any DNA sequence may be selected. According to the embodiment described in Example 5, the vector can express simultaneously a plurality of genes that are placed with an IRES between each two genes. According to the embodiment described in Example 6, a DNA sequence encoding a fusion protein can be selected for the purpose of facilitating the detection of transfected cells or for other various purposes.

As a specific example of a gene of interest for reversibly immortalizing cells, a combination of human telomerase gene (hTERT) and Bmi-1 gene may be given (Salmon et al., *Molecular Therapy*, 2:404–414). It has been shown that by transfecting these genes into human myoblast cells, cell proliferation becomes possible while retaining the normal karyotype (Cudre-Mauroux et al., *Molecular Therapy*, Vol. 3, p. S280, No. 795). On the other hand, when a combination of hTERT and SV40 large T antigen gene is used, cell proliferation becomes possible but cells exhibit abnormal karyotype (Cudre-Mauroux et al., supra). Thus, for the purpose of temporarily proliferating cells, it is preferable to use a combination of hTERT and Bmi-1 as a first gene of interest to be placed in the vector of the invention. When these genes are placed with an IRES between them, they can be expressed simultaneously.

Further, the vector of the invention was applied to hepatocytes and cord blood CD34 positive cells as described in Examples 5 and 6 to thereby demonstrate that the vector of the invention is useful in various cell types. The vector of the invention is applicable to ex vivo and in vivo acquisition of proliferative property in wide varieties of functional cells and organs including skin, cartilage, bone, blood, blood vessels, nerve, cardiac muscle, liver and pancreatic islets, induction of differentiation into cells of a specific lineage, control of differentiation/dedifferentiation, control of immortalization/deimmortalization, and tissue formation. As a target cell, embryonic stem cells, adult stem cells, or somatic cells under differentiation or finally differentiated may be used. The vector of the invention is capable of transferring any desired gene into cells ex vivo and in vivo for the purpose of medical treatment, and thus applicable to the so-called gene therapy. It is also possible to use the vector of the invention in the creation of transgenic animals or knockout animals. The vector of the invention is extremely useful in the creation of conditional transgenic animals or conditional knockout animals since any gene of interest transferred thereinto with the vector can be excised, or expression of one gene of interest can be switched to expression of other gene of interest by administering a low molecular weight compound to the resultant animals. These animals are useful in in vivo analysis of genes, particularly, functional analysis of those genes working at developmental stages in the adult body. Those cells and animals into which genes have been transferred using the vector of the invention are also included in the scope of the invention.

Hereinbelow, the present invention will be described in more detail with reference to the following Examples. However, these Examples are provided only for the purpose of explanation, and should not be construed as limiting the technical scope of the invention. The genetic engineering techniques used in the following Examples are those practiced routinely by those skilled in the art. For experimental instructions, see J. Sambrook, D. W. Russel et al. (eds), *Molecular Cloning: A Laboratory Manual, Third Edition*, (2001), Cold Spring Harbor Laboratory Press. The retrovirus vector of the invention can be designed with reference to J. M. Coffin, S. H. Hughes and H. E. Varmus (eds), *Retroviruses*, Cold Spring Harbor Laboratory Press (Chapter 9 is particularly useful).

EXAMPLE 1

Construction of Plasmid
pMSCV/lox-DsRed-Cre-BI-rtTA-lox-EGFP (1) Ligation of a Cre Recombinase Gene to a PolyA Signal Sequence First, the following DNA fragments, (a), (b) and (c), are prepared: (a) an approx. 1 kilobase pair (kb) DNA fragment containing a gene encoding Cre recombinase (Cre), obtainable by digesting plasmid pMC-Cre (received from Dr. Klaus Rajewsky, Cologne University; *Cell* 73:1155, 1993) with restriction enzymes Not I and Aor51H I; (b) an approx. 180 base pair (bp) DNA fragment containing a virus SV40-derived polyA signal region, obtainable by digesting plasmid pEGFP-1 (available from Clontech) with restriction enzymes Dra I and Afl II; and (c) an approx. 5.4 kb DNA fragment obtainable by digesting plasmid pcDNA3.1 (available from Invitrogen) with restriction enzymes Afl II and Not I. Subsequently, these DNA fragments, (a), (b) and (c), are subjected to ligation. Thus, the obtained plasmid is composed of an approx. 1.2 kb DNA fragment and an approx. 5.4 kb DNA fragment when digested with restriction enzymes Afl II and Not I. That is, this plasmid has a construction where a DNA fragment comprising a DNA sequence composed of a Cre recombinase gene and a polyadenylation signal ligated thereto is inserted into the Afl II-Not I recognition sites in the multi-cloning site of plasmid pcDNA3.1. Upon confirmation of this structure, the resultant plasmid is designated pcDNA/CrepA.

(2) Ligation of a Tetracycline-Responsive Bidirectional Element/Promoter (BI) to a Reverse Tetracycline-Controlled Activator (rtTA) Gene First, the following DNA fragments, (a), (b) and (c), are prepared: (a) an approx. 1.0 kb DNA fragment containing a gene encoding a reverse tetracycline-controlled activator (rtTA), obtainable by preparing an approx. 1.1 kb PCR (polymerase chain reaction) product by performing a PCR using plasmid pRevTet-On (available from Clontech) as a template and synthetic oligo DNAs, RTTA1S and RTTA2A, as primers, ligating this PCR product into plasmid pCR2.1 (available from Invitrogen) to obtain pCR/rtTA, and then digesting this plasmid with restriction enzymes Bgl I and Xho I; (b) an approx. 560 kb DNA fragment containing a tetracycline-responsive bidirectional element/promoter (BI), obtainable by digesting plasmid pBI (available from Clontech) with a restriction enzyme Not I and then partially digesting with a restriction enzyme Bgl I; and (c) an approx.

2.9 kb DNA fragment obtainable by digesting plasmid pBluescript II KS(+) (available from Stratagene) with restriction enzymes Not I and Xho I. Subsequently, these DNA fragments (a), (b) and (c) are subjected to ligation. Since the thus obtained plasmid yields an approx. 1.6 kb DNA fragment and an approx. 2.9 kb DNA fragment when digested with restriction enzymes Not I and Xho I, it is confirmed that this plasmid has a structure in which a DNA fragment comprising a DNA sequence composed of BI and rtTA gene ligated thereto is inserted into the Not I-Xho I recognition sites in the multi-cloning site of plasmid pBluescript II KS(+). Upon this confirmation, the plasmid is designated pBS/BI-rtTA.

(3) Preparation of a DNA Unit, Cre-BI-rtTA Construct, and Deletion of the Not I-EcoR I Recognition Sites An approx. 6.6 kb DNA fragment obtainable by digesting the plasmid pcDNA/CrepA constructed in (1) above with restriction enzymes Not I and Xho I, and an approx. 1.6 kb DNA fragment obtainable by digesting the plasmid pBS/BI-rtTA constructed in (2) above with restriction enzymes Not I and Xho I are subjected to ligation. Since the resulting plasmid yields an approx. 2.8 kb and an approx. 5.4 kb DNA fragments, it is confirmed that this plasmid has a structure where a DNA unit construct, Cre-BI-rtTA, is inserted into the Afl II-Xho I recognition sites in the multi-cloning site of plasmid pcDNA3.1(+). Upon this confirmation, this plasmid is designated pcDNA/Cre-BI-rtTA. Subsequently, pcDNA/Cre-BI-rtTA is digested with restriction enzymes Not I and EcoR I, blunt-ended with T4 DNA polymerase, and self-ligated. As a result, the Not I, Pst I and EcoR I recognition sites that were present between Cre and BI are deleted. The resultant plasmid is designated pcDNA/Cre-BI-rtTA(ΔNE).

(4) Addition of a loxP Sequence (Restriction Enzyme Recognition Site) to a DNA Encoding Green Fluorescent Protein (EGFP)

An approx. 790 kb PCR product is obtained by performing a PCR using plasmid pEGFP-1 (available from Clontech) as a template and synthetic oligo DNAs, LOXEGFP1S EGFPHIND2A, as primers. This PCR product is ligated into plasmid pCR2.1 to obtain plasmid pCR/loxEGFP.

(5) Addition of a loxP Sequence (Restriction Enzyme Recognition Site) to a DNA Encoding Red Fluorescent Protein (DsRed)

An approx. 740 bp PCR product is obtained by performing PCR using plasmid pDsRed1-N1 (available from Clontech) as a template and synthetic oligo DNAs, LOXRED1S and RED2AMOD, as primers. This PCR product is ligated into plasmid pCR2.1 to obtain plasmid pCR/loxRed.

(6) Integration of the DNA Fragment loxEGFP into Plasmid pMSCVneo

An approx. 5.2 kb DNA fragment containing the 5' LTR, packaging signal (Ψ) and 3' LTR of a mouse stem cell virus MSCV retrovirus vector, obtained by digesting plasmid pMSCVneo (available from Clontech) with restriction enzymes Xho I and Hind II, and an approx. 790 bp DNA fragment obtained by digesting the plasmid pCR/loxEGFP from (4) above with restriction enzymes Xho I and Hind III are subjected to ligation to thereby prepare plasmid pMSCV/loxEGFP.

(7) Preparation of Plasmid pMSCV/lox-DsRed-Cre-BI-rtTA-lox-EGFP

The following three DNA fragments (a) to (c) are subjected to ligation: (a) an approx. 6.0 kb DNA fragment obtained by digesting the plasmid pMSCV/loxEGFP from (6) above with restriction enzymes EcoR I and Xho I; (b) an approx. 740 bp DNA fragment obtained by digesting the plasmid pCR/loxRed from (5) above with restriction enzymes EcoR I and Afl II; and (c) an approx. 2.8 kb DNA fragment obtained by digesting the plasmid pcDNA/Cre-BI-rtTA(ΔNE) from (3) above with restriction enzymes Afl II and Xho I. The resultant plasmid is composed of an approx. 4.3 kb and an approx. 5.2 kb DNA fragments when digested with restriction enzymes EcoR I and Not I. Also, when its nucleotide sequence is determined with a DNA sequencer, this plasmid has a structure in which DNA units of 5' LTR, Ψ (packaging signal), loxP, DsRed, Cre, BI, rtTA, loxP, EGFP and 3' LTR are ligated in this order. Upon confirmation of these points, this plasmid is designated pMSCV/lox-DsRed-Cre-BI-rtTA-lox-EGFP.

(8) Preparation of Control Plasmids

As a plasmid for expressing EGFP, the plasmid pMSCV/loxEGFP prepared in (6) above was used. As a plasmid for expressing DsRed, plasmid pMSCV/loxDsRed is prepared by ligating the following two DNA fragments: an approx. 1.6 kb DNA fragment obtained by digesting the plasmid pMSCV/lox-DsRed-Cre-BI-rtTA-lox-EGFP with restriction enzymes EcoR I and BamH I and an approx. 5.2 kb DNA fragment obtained by digesting plasmid pMSCVneo with the same restriction enzymes.

EXAMPLE 2

Preparation of Retrovirus Vectors

The plasmid pMSCV/ox-DsRed-Cre-BI-rtTA-lox-EGFP and the control plasmids prepared in Example 1 are transfected into a packaging cell strain BOSC23 (received from Dr. David Baltimore, California Institute of Technology; *Proc. Natl. Acad. Sci. USA,* 90:8392, 1993) to prepare retrovirus vectors.

BOSC23 cells ($2\times10^6$ cells/dish) are cultured in 4 ml of 10% FCS (fetal calf serum)-containing Dulbecco's modified Eagle's medium (DME) in 60 mm φ dishes (Falcon 3002) placed in a 5% $CO_2$ incubator at 37° C. for 18–24 hr. Immediately before transfection, the medium is replaced with 4 ml of 10% FCS-containing DME containing 25 μM chloroquine. The transfection is performed using Transfection MBS Mammalian Transfection Kit (Stratagene) in accordance with the instructions written in the attached protocol.

Briefly, 8 μg of DNA from the above-mentioned plasmid is diluted with distilled water to give a final volume of 450 μl in a 5 ml polystyrene tube (Falcon 2054). Subsequently, 50 μl of 2.5 M $CaCl_2$ and 500 μl of 2-fold concentrated BBS (physiological saline containing a buffer N,N-bis(2-hydroxyethyl)-2-aminoethanesulfonic acid) (pH 6.95) are added thereto and mixed. The resultant mixture is left at room temperature for 15 min. In the meantime, the culture supernatant is removed from the cultured cells by suction, and the cells are washed in PBS (phosphate-buffered physiological saline) twice, followed by addition of 5 ml of 5% FCS-containing DME. Subsequently, 500 μl of the DNA suspension prepared above is added to the cells and mixed in a swirling manner. The resultant mixture is incubated in a 5% $CO_2$ incubator at 37° C. for 3 hr. After removal of the culture supernatant, the cells are washed in PBS three times. After addition of 5 ml of 10% FCS-containing DME, the cells are cultured in a 5% $CO_2$ incubator at 37° C. Forty-eight hours, 60 hours and 72 hours after the start of this cultivation, the culture supernatant containing retrovirus is recovered. The culture supernatant is passed through a 0.45 μm disc filter (Acrodisc; Gelman Sciences) to remove the cells mixed therein, placed in dry ice-cooled tubes (Falcon 2070) and stored in a deep freezer at −70° C.

The retrovirus vectors obtained by transfecting the plasmids pMSCV/lox-DsRed-Cre-BI-rtTA-lox-EGFP, pMSCV/loxEGFP and pMSCV/loxDsRed into BOSC23 cells are designated MSCV/lox-DsRed-Cre-BI-rtTA-lox-EGFP, MSCV/loxEGFP and MSCV/loxDsRed, respectively.

EXAMPLE 3

Retrovirus Vector-Infection of Cells and Detection of Fluorescent Proteins

NIH3T3 cells ($5 \times 10^5$ cells) (received from RIKEN GenBank) are cultured overnight in 10% FCS-containing DME in a 100 φ culture plate (Falcon 3003). After removal of the culture supernatant, a mixture composed of 1 ml of the retrovirus vector-containing supernatant obtained in Example 2, 10 μl of 5 mg/ml polybrene solution and 2 ml of fresh medium is added to the cells. Then, the cells are incubated for 3 hr and, after addition of 7 ml of fresh medium, incubated for another 9 hr to thereby infect them with the retrovirus vector. Subsequently, these infection operations are repeated three times, followed by cultivation of the cells for 48 hours. The resultant cells are observed with a fluorescent microscope (Olympus IX-70). Approx. 60% of those cells infected with the retrovirus vector MSCV/lox-DsRed-Cre-BI-rtTA-lox-EGFP or MSCV/loxDsRed emit red fluorescence from DsRed, and approx. 60% of those cells infected with the retrovirus vector MSCV/lox-EGFP emit green fluorescence from EGFP. The remaining approx. 40% are cells that do not emit fluorescence, i.e. cells not infected with the relevant retrovirus vector.

After replacement of the medium with fresh medium containing 1 μg/ml doxycycline, these cells are cultured for another 48 hr and then observed with a fluorescent microscope. Approx. 60% of the cells infected with the retrovirus vector MSCV/lox-DsRed-Cre-BI-rtTA-lox-EGFP emit green fluorescence, and no cells emitting red fluorescence are observed in this cell population. Approx. 60% of the cells infected with the retrovirus vector MSCV/loxDsRed remain in the same state, i.e., emitting red fluorescence. From these results, it is confirmed that expression of Cre recombinase is induced by doxycycline, resulting in excision of the loxP stuffer.

EXAMPLE 4

Confirmation of the Stuffer Excision Sites by PCR on Genomic DNA

In order to determine whether the stuffer excision by Cre recombinase is performed in a loxP sequence-specific manner, genomic DNA is extracted from the cells before and after the induction by doxycycline and subjected to PCR using PCR primers specific to the DNA sequences flanking the stuffer.

Briefly, genomic DNA is extracted from the cells in a 100 mm φ culture plate using QIAGEN Blood & Cell Culture DNA kit (Qiagen) in accordance with the protocol attached to the kit. The resultant genomic DNA is digested with restriction enzymes EcoR I and Not I. As PCR primers, a forward primer is prepared that is an oligo DNA comprising a part of the Ψ sequence, and a reverse primer is prepared that is an oligo DNA comprising a part of the sequence complementary to the DNA sequence encoding EGFP. Then, PCR is performed using the above-described digested genomic DNA as a template. The resultant PCR product is subjected to agarose gel electrophoresis to examine its size.

As a result, the sample taken before the induction by doxycycline generates an approx. 4.1 kb product, and the sample taken after the induction an approx. 500 bp product. Thus, it is confirmed that the latter is shorter than the former by approx. 3.6 kb that corresponds to the length of the loxP stuffer. Further, the PCR product is sub-cloned into plasmid pCR2.1, followed by determination of the DNA sequence with a DNA sequencer. As a result, it is confirmed that the stuffer sequence is excised by the induction caused by doxycycline in a loxP sequence-specific manner.

EXAMPLE 5

Reversible Immortalization of Mouse Hepatocytes

By inserting IVS (synthetic intron)-added IRES (internal ribosome entry site derived from encephalomyocarditis virus) and the SV40 large T gene between the DsRed gene and the Cre gene in plasmid pMSCV/lox-DsRed-Cre-BI-rtTA-lox-EGFP, this plasmid is modified so that it can express DsRed and SV40 large T bicistronically. Briefly, the following three DNA fragments are subjected to ligation: an approx. 940 bp DNA fragment obtained by digesting plasmid pIRESneo (available from Clontech) with restriction enzymes BamH I and Sma I, an approx. 2.3 kb DNA fragment obtained by digesting the SV40 large T gene (available from RIKEN GenBank) with restriction enzymes EcoR V and Not I, and an approx. 2.9 bp DNA fragment obtained by digesting plasmid pBluescript KS II (+) with restriction enzymes BamH I and Not I. The resultant plasmid is digested with restriction enzymes BamH I and Not I to obtain an approx. 3.2 kb fragment, which is then blunt-ended. The resultant fragment is digested with a restriction enzyme EcoT22 I and blunt-ended. The resultant fragment is ligated into dephosphorylated plasmid pMSCV/lox-DsRed-Cre-BI-rtTA-lox-EGFP to obtain a plasmid. The nucleotide sequence of this plasmid is determined with a DNA sequencer to confirm that this plasmid has a structure in which DNA units of 5' LTR, Ψ, loxP, DsRed, IRES, SV40 large T, Cre, BI, rtTA, loxP, EGFP and 3' LTR are ligated in this order.

This plasmid is designated pMSCV/lox-DsRed-IRES-SV40T-Cre-BI-rtTA-lox-EGFP. This plasmid is transfected into BOSC23 cells in the same manner as described in Example 2 to thereby obtain retrovirus vector MSCV/lox-DsRed-IRES-SV40T-Cre-BI-rtTA-lox-EGFP.

The abdomens of BALB/c mice anesthetized with Nembutal are opened, followed by cannulation of portal veins. The mice are exsanguinated using PBS. After perfusion with Hanks' solution containing 0.05% collagenase, livers are removed. The livers are cut into pieces, dispersed in a vortex mixer, and centrifuged at a low speed (50 G). The resultant cells are suspended and filtered through a 150 μm nylon filter to thereby obtain mouse hepatocytes. These cells are cultured overnight in 10% FCS-supplemented DME on collagen-coated 24-well plates. After removal of the culture supernatant, 1 ml of BOSC23 culture supernatant containing the retrovirus vector MSCV/lox-DsRed-IRES-SV40T-Cre-BI-rtTA-lox-EGFP and 1 μl of 5 mg/ml polybrene solution were added to the cells, which are then cultured for 12 hr. Further, these operations were repeated three times.

Subsequently, the medium is replaced with fresh 10% FCS-supplemented DME, followed by cultivation of the cells for 48 hr. The resultant cells are observed with a fluorescent microscope. It is observed that approx. 60% of the cells emit red fluorescence from DsRed. Approx. 60% of those cells that have been infected with the control retrovirus vector MSCV/loxDsRed in the same manner also emit red fluorescence. These two populations of mouse hepatocytes are cultured for another one week while replacing the medium in every two days.

It is observed with a fluorescent microscope that the mouse hepatocytes infected with the retrovirus vector MSCV/lox-DsRed-IRES-SV40T-Cre-BI-rtTA-lox-EGFP have proliferated to such an extent that they cover the cell adhesive surface of the 24-well plate almost completely and that almost 100% of the cells emit red fluorescence. On the other hand, no viable cells can be confirmed in the hepatocytes infected with the control vector when observed after Trypan Blue staining.

This hepatocyte cell strain immortalized by infection with the retrovirus vector-MSCV/lox-DsRed-IRES-SV40T-Cre-BI-rtTA-lox-EGFP is designated mHep1. When mHep1 cells are dispersed by collagenase treatment and subcultured in 60 mm culture plates with replacement of the medium in every two days, it is observed that these cells proliferate with an average doubling time of about 48 hr. A part of this mHep1 cell strain is seeded on a 60 mm culture plate and grown to confluency. Then, almost 100% of cells emit red fluorescence under a fluorescent microscope. These cells are cultured for another 48 hr after replacement of the medium with fresh medium containing 1 µg/ml doxycycline, followed by observation under a fluorescent microscope. No cells emitting red fluorescence are observed; every cell emits green fluorescence. These cells are designated mHep1-dox and cultured for another 1 week with replacement of the medium in every two days. As a result, it is confirmed that these cells do not proliferate.

mRNA is extracted from mHep1-dox cells using Quick Prep Micro mRNA Purification Kit (Amersham Pharmacia), followed by synthesis of a single-stranded cDNA therefrom using First-Strand cDNA Synthesis Kit (Amersham Pharmacia). When the resultant cDNA is amplified by PCR, a part of the DNA sequence for mouse serum albumin (GenBank Accession No. MMU011418) and also a part of the DNA sequence for mouse blood coagulation factor X (GenBank Accession No. BC003877) are detected, but SV40 large T is not detected. Therefore, it can be confirmed that hepatocytes are reversibly immortalized by the retrovirus vector MSCV/lox-DsRed-IRES-SV40T-Cre-BI-rtTA-lox-EGFP.

EXAMPLE 6

Reversible Control of Differentiation in Cord Blood CD34 Positive Cells

For the purpose of ex vivo expansion of cord blood CD34 positive cells, a gene for a dominant negative retinoic acid receptor α (RARα) having a differentiation inhibitory effect on hematopoietic cells (Tsai et al., *Gene & Development* 6: 2258–2269) is transfected into cord blood CD34 positive cells, and the transfected cells are allowed to proliferate under a temporarily differentiation-inhibited state. Subsequently, these cells are restored to cells having normal hematopoietic functions by deleting the above-described gene by induction using a low molecular weight compound.

Briefly, a DNA encoding the amino acids from the amino terminal to position 403 of RARα (received from Dr. Ronald Evans, Salk Institute; GenBank Accession No. HSRRA) is inserted between lox and DsRed in the plasmid pMSCV/lox-DsRed-IRES-SV40T-Cre-BI-rtTA-lox-EGFP to thereby prepare plasmid pMSCV/lox-RARA403DsRed-IRES-SV40T-Cre-BI-rtTA-lox-EGFP containing, instead of DsRed gene, a DNA encoding a fusion protein composed of a truncated form of RARα fused to DsRed.

By transfecting this plasmid into an amphotropic packaging cell strain Bing (available from American Type Culture Collection) in the same manner as described in Example 2, retrovirus vector MSCV/lox-RARA403DsRed-Cre-BI-rtTA-lox-EGFP (hereinafter, abbreviated to "MSCV/RA403") is obtained.

Monocyte fraction is collected from cord blood using Ficoll Paque Plus (Amersham Pharmacia). Then, CD34 positive fraction is obtained using a CD34 hematopoietic progenitor cell separation system (Dynal). Both procedures are according to the instructions attached to the products.

CD34 positive cells ($1 \times 10^4$) are suspended in 1 ml of the Bing culture supernatant containing the retrovirus vector MSCV/RA403 or a control vector, and added to each well of a 24-well plate whose culture surface is precoated with 8 µg of RetroNectin (Takara). A cytokine cocktail (1 µl) containing 1 µl/mg human interleukin-3 (IL-3; PeproTech), 10 µl/mg human interleukin-6 (IL-6; PeproTech) and 100 µl/mg human stem cell factor (SCF; PeproTech), and 1 µl of 5 mg/ml polybrene solution are added thereto, and cells are cultured for 12 hr. Further, these operations are repeated three times. Subsequently, the medium is replaced with 1 ml of fresh DME supplemented with 10% FCS and 1 µl of the cytokine cocktail, and cells are cultured for another 48 hr. In the cell populations infected with the retrovirus vector MSCV/RA403 and the control vector MSCV/loxRsRed, respectively, approx. 30% is observed DsRed positive under a fluorescent microscope. Subsequently, the cells are cultured for another 14 days in the presence of cytokines with replacement of the medium in every two days. Then, the cells are cultured for another 48 hr after replacement of the medium with fresh medium containing 1 µg/ml doxycycline. The resultant cells are transferred into a hematopoietic colony assay medium (MethoCul™GF; StemCell Technologies), in which a hematopoietic colony assay is conducted for two weeks.

As a result, it is observed that all the hematopoietic colonies of the retrovirus vector MSCV/RA403-infected cells are EGFP positive and that they include a great number of immature, mix colonies. On the other hand, no immature, mix colonies can be detected in the control vector-infected cells. These results confirm the following: (1) by temporarily introducing the gene for dominant negative retinoic acid receptor ac into cord blood CD34 positive cells, these cells are allowed to proliferate while the differentiation of undifferentiated hematopoietic cells are inhibited; and (2) after deletion of the above-described gene, these cells still retain the innate function of undifferentiated hematopoietic cells, i.e., the ability to form hematopoietic colonies.

The abbreviations used in the Figures have the following meaning.
SS-Rec: site-specific recombinase gene
TS: target DNA sequence for a site-specific recombinase
Pro: constitutive promoter
LTR: long terminal repeat of a retrovirus vector
lox: loxP sequence
Ind. Pro: inducible promoter
Cre: Cre recombinase gene
pA: polyadenylation signal sequence
Tet Pro: Tet-responsive promoter
rtTA: reverse Tet transactivator
IRES-Neo: internal ribosome entry site from encephalomyocarditis virus and neomycin resistance gene
BI: low molecular weight compound-responsive bidirectional promoter
TA: transactivator gene
Pmin: minimal promoter
TetO: Tet operator sequences
(r)tetR: (reverse) Tet repressor gene VP16: herpes simplex virus VP16 gene
ZFHD1: binding sites for ZFHD1 protein
GAL4: yeast GAL4 gene
HPR-LBD: ligand binding domain of human progesterone receptor
EcR: ecdysone receptor
Pip: *Streptomyces* Pip gene
$P_{PTR}$: binding sites for Pip protein

EFFECT OF THE INVENTION

When integrated into the genome of a mammalian cell, the single gene vector of the invention can alter the nature of the cell by transferring any gene of interest thereinto. The transferred gene can be excised at any time by administering to the mammal a low molecular weight compound. Thus, the vector of the invention is extremely useful in gene therapy and the like. Also, by introducing a gene that inhibits differentiation into stem cells and progenitor cells and excising the gene using the vector of the invention, it is possible to allow these cells to proliferate while retaining the undifferentiated state. Further, by introducing an immortalizing gene into terminally differentiated functional cells and excising the gene using the vector of the invention, it is possible to allow these cells to proliferate while retaining their functions. Thus, the obtained cells are useful in cell transplantation and regenerative therapy. Furthermore, the single gene vector of the invention is extremely useful in the creation of conditional transgenic and knockout animals.

What is claimed is:

1. A single vector comprising a gene arrangement satisfying all of the following requirements (1) to (4) when inserted into the genome of a mammalian cell:
   (1) a DNA encoding a low molecular weight compound-controlled transactivator placed on one side of a bidirectional promoter responsive to said low molecular weight compound, and a DNA encoding a site-specific recombinase and a polyadenylation signal sequence placed on the other side of said promoter, wherein said low molecular weight compound is at least one selected from the group consisting of tetracycline, doxycycline, FK506, RU486, ecdysone and streptogramin;
   (2) a gene of interest placed between two target sites of said site-specific recombinase;
   (3) the gene of interest placed under the control of a promoter capable of directing expression of said gene in mammalian cells, and the DNA encoding said site-specific recombinase placed in such a manner that a transcript from said promoter includes a transcript of the site-specific recombinase DNA, and that the latter transcript and another transcript of the site-specific recombinase DNA from the bidirectional promoter of (1) form a double-stranded RNA;
   (4) polyadenylation signal sequences which are capable of adding poly(A) to a transcript of the low molecular weight compound-controlled transactivator and a transcript from the promoter capable of directing expression in mammalian cells, respectively.

2. The vector according to claim 1, wherein the vector has the following gene arrangement:
   5'—Target site of the site-specific recombinase—Promoter capable of directing expression in mammalian cells—Gene of interest—Polyadenylation signal sequence placed in the opposite orientation—DNA encoding the site-specific recombinase in the opposite orientation—Low molecular weight compound-responsive bidirectional promoter—DNA encoding the low molecular weight compound-controlled transactivator—Polyadenylation signal sequence—Target site of the site-specific recombinase—3'.

3. The vector according to claim 1, wherein the vector has the following gene arrangement:
   5'—Promoter capable of directing expression in mammalian cells—Target site of the site-specific recombinase—Gene of interest—Polyadenylation signal sequence placed in the opposite orientation—DNA encoding the site-specific recombinase in the opposite orientation—Low molecular weight compound-responsive bidirectional promoter—DNA encoding the low molecular weight compound-controlled transactivator—Target site of the site-specific recombinase—Polyadenylation signal sequence—3'.

4. The vector according to claim 1, wherein the vector has the following gene arrangement:
   5'—Promoter capable of directing expression in mammalian cells—Target site of the site-specific recombinase—Gene of interest—Target site of the site-specific recombinase—Polyadenylation signal sequence placed in the opposite orientation—DNA encoding the site-specific recombinase in the opposite orientation—Low molecular weight compound-responsive bidirectional promoter—DNA encoding the low molecular weight compound-controlled transactivator—Polyadenylation signal sequence—3'.

5. The vector according to any one of claims 1, 2, 3, or 4, wherein the vector is a retroviral vector.

6. The vector according to any one of claims 1, 2, 3, or 4, wherein the low molecular weight compound is tetracycline or doxycycline, and the low molecular weight compound-controlled transactivator is a reverse tetracycline transactivator.

7. The vector according to any one of claims 1, 2, 3, or 4, wherein the site-specific recombinase is Cre recombinase, and the target site of said site-specific recombinase is loxP.

8. The vector according to any one of claims 1, 2, 3, or 4, wherein the site-specific recombinase is FLP recombinase, and the target site of said site-specific recombinase is FRT.

9. The vector according to any one of claims 1, 2, 3, or 4, wherein the gene of interest is human telomerase gene and/or Bmi-1 gene.

10. The vector according to any one of claims 1, 2, 3, or 4, wherein a second gene of interest is placed 3' to one of the two target sites of the site-specific recombinase located closer to the 3' end of the vector DNA.

11. The vector according to claim 10, wherein said vector has the following gene arrangement:
    5'—LTR—Target site of the site-specific recombinase—1st Gene of interest—Polyadenylation signal sequence placed in the opposite orientation—DNA encoding the site-specific recombinase in the opposite orientation—Low molecular weight compound-responsive bidirectional promoter—DNA encoding the low molecular weight compound-controlled transactivator—Target site of the site-specific recombinase—2nd Gene of interest—LTR-3'.

12. An isolated mammalian cell which is transduced with the vector according to claim 1.

* * * * *